United States Patent [19]
Kornacker

[11] Patent Number: 6,051,381
[45] Date of Patent: Apr. 18, 2000

[54] PROKARYOTIC TWO-HYBRID SYSTEM

[76] Inventor: Michael G. Kornacker, 110 Nassau St., Princeton, N.J. 08543

[21] Appl. No.: 08/987,965

[22] Filed: Dec. 10, 1997

Related U.S. Application Data

[60] Provisional application No. 60/032,821, Dec. 11, 1996.

[51] Int. Cl.⁷ .............................. C12Q 1/68; C12N 1/21; C12N 15/11; C12N 15/70
[52] U.S. Cl. ...................... 435/6; 435/252.3; 435/252.33; 435/320.1; 536/23.1; 536/24.1
[58] Field of Search ...................... 435/6, 252.3, 252.33, 435/320.1; 536/23.1, 23.2, 23.7, 24.1

[56] References Cited

PUBLICATIONS

Jappelli et al. (1996) J. Mol. Biol. 259:575–8.
Marchetti et al (1995) J. Mol. Biol. 248:541–50.
Schmidt–Dorr et al. (1991) Biochem. 30:9657–64.
Dove et al. (1997) Nature 386:627–30.
Nakamura et al. (1972) J. Bacteriol. 110:329–35.
Higgins (1993) Curr. Opin. in Cell Biol. 5:684–687.
Allen et al. (1995) Trends in Biochem. Sci. 20:511–16.
Fields et al. (1989) Nature 340:245–6.
Liuzzi et al. (1994) nature 372:695–8.
Yan et al. (1995) Cancer Res. 55:3569–75.
Gibbs et al. (1994) Cell 79:193–198.
Luban et al. (1995) Curr. Opin. in Biotech. 6:59–64.
Fields et al. (1994) Trends Genet. 10:8:286–292.
Hollis et al. (1988) Proc. Natl. Acad. Sci. USA 85:5834–8.
Schleif (1996) in *Echerichia coli* and *Salmonella Typhimurium* Cellular and Mulecular Biology (Neidhardt, ed.) ASM Press, Washington, D.C. 1300–9.
Bustos & Schleif (1993) Proc. Natl. Acad. Sci. USA 90:5638–42.
Kim & Little (1992) Science 255:203–6.
Reeder & Schleif (1993) J. Mol. Biol. 231:205–218.
Elledge & Davis (1989) Genes & Dev. 3:185–197.
Mueller et al. (1996) J. Mol. Biol. 257:21–9.
Choy & Adhya (1992) Proc. Natl. Acad. Sci. USA 89:11264–8.
Huo et al. (1988) Proc. Natl. Acad. Sci. USA 85:5444–8.
Yang & Nash (1994) Proc. Natl. Acad. Sci 91:12183–12187.
Nash (1990) Trends Biochem. Sci. 15:222–7.
Pratt et al. (1996) Mol. Microbiol. 20:911–7.
Hoover et al. (1990) Cell 63:11–22.
Halazonetis et al. (1988) Cell 55:917–24.
Lee & Schleif (1989) Proc. Natl. Acad. Sci. 86:476–480.
Ryseck et al. (1990) Oncogene 5:1091–3.
Lewis et al. (1994) J. Miol. Biol. 241:507–23.
Golemis & Brent (1992) Mol. Cell Biol. 12:3006–14.
Huibregtse et al. (1991) EMBO J. 10:4129–35.
Rippe et al. (1995) Trends in Biochem. Sci. 20:500–06.
Wang & Giaever (1988) Science 240:300–06.
Nickerson & Achberger (1995) J. Bacteriol. 177:5756–61.
Chatterjee et al. (1997) Proc. Natl. Acad. Sci. USA 94:2957–62.
Giffard & Booth (1988) Mol. Gen. Genet. 241:148–152.
Muller & Sapp (1996) zirology 219:247–56.
Girling et al. (1993) Nature 352:83–87.
Kadesch (1993) Cell Growth & Different. 4:49–55.
Eustance et al. (1994) J. Mol. Biol. 242:330–338.
Cleland (1993) in Protein Folding: in Vivo and in Vitro, ed. J. Cleland (ACS) pp. 1–21.
Wall (1996) Bio Techniques 20:690–693.
Davis & Jacob (1968) J. Mol. Biol. 36:413–27.

*Primary Examiner*—Robert A. Schwartzman
*Attorney, Agent, or Firm*—Joseph M. Sorrentino; Timothy J. Gaul

[57] ABSTRACT

A two-hybrid system that can detect homo- and heterodimeric protein interactions in *E. coli* and other cells. This system is useful for the same applications as a yeast two-hybrid system; i.e. interaction cloning, mapping protein interaction domains, analyzing protein interactions, detecting protein interactions and detecting modulators thereof. The invention concerns a prokaryotic host cell comprising:
(a) a fusion protein having (i) a first DNA-binding domain and (ii) a first interacting domain;
(b) a fusion protein having (i) a second DNA-binding domain and (ii) a second interacting domain capable of binding to the first interacting domain; and
(c) a nucleic acid molecule having a reporter gene operatively linked to (i) a promoter, (ii) a first operator site capable of binding to the first DNA-binding domain, located upstream of the promoter, and (iii) a second operator site capable of binding the second DNA-binding domain, located downstream of the promoter of the reporter gene;
wherein binding of the first interacting domain to the second interacting domain is signaled by altered expression of the reporter gene.

24 Claims, 7 Drawing Sheets

```
                                        I1                                                      -35                                                 -10
TAGCATTTTTATCCATAAGATTAGCATTTTTATCCATAGATCCTGGTACCGAATTCATGGATCCTACCTGAC
+1             Sacl           Xbal
GCTTTTATCGGAGCTCTCTACTGTTTCTAGATACCCGTTTTTTGGATGGGAGTGAAACG
                                    HindIII
ATGGCGATTGCAATTGGAATTCCAAGCTT-----LacZ
```

LexAOp for Xbal:
Xbal-Sacl ATATACAGTA ATATACAGTA ATATACAGTA C-Sacl-Xbal

LexAOp for HindIII:
HindIII-T-Xbal-Sacl ATATACAGTA ATATACAGTA ATATACAGTA ATATACAGTA C-Sacl-Xbal-A-HindIII Lambda H' IHF site for Sacl:
Sacl-ATAAAAAGCATTGCTTATCAATTTGTTGCAAGG-Sacl

FIG. 2A

SEQUENCE LISTING

<160> NUMBER OF SEQ ID NOS: 15

<210> SEQ ID NO 1
<211> LENGTH: 160
<212> TYPE: DNA
<213> ORGANISM: Escherichia coli

<400> SEQUENCE: 1
tagcattttt atccataaga ttagcatttt tatccataga tcctggtacc gaattcatgg      60
atcctacctg acgctttta tcggagctct ctactgtttc tagatacccg ttttttttgga    120 tggagtgaaa cgatggcgat tgcaattgga atccaagctt                          160

<210> SEQ ID NO 2
<211> LENGTH: 10
<212> TYPE: DNA
<213> ORGANISM: Escherichia coli

<400> SEQUENCE: 2

-continued tactgtatat                                                                                        10

<210> SEQ ID NO 3
<211> LENGTH: 41
<212> TYPE: DNA
<213> ORGANISM: Escherichia coli
<220> FEATURE:
<221> NAME/KEY: misc_binding
<222> LOCATION: (1)..(41)
<223> OTHER INFORMATION: n represents any nucleotide

<400> SEQUENCE: 3
tnnnnnnatn anntnnantn aaatcaanaa gttannnnnn a                                                     41

<210> SEQ ID NO 4
<211> LENGTH: 124
<212> TYPE: PRT
<213> ORGANISM: Escherichia coli

<400> SEQUENCE: 4

Glu Ser Leu His Pro Pro Met Asp Asn Arg Val Arg Glu Ala Cys Gln
 1               5                  10                  15

Tyr Ile Ser Asp His Leu Ala Asp Ser Asn Phe Asp Ile Ala Ser Val
            20                  25                  30

Ala Gln His Val Cys Leu Ser Pro Ser Arg Leu Ser His Leu Phe Arg
        35                  40                  45

Gln Gln Leu Gly Ile Ser Val Leu Ser Trp Arg Glu Asp Gln Arg Ile
    50                  55                  60

Ser Gln Ala Lys Leu Leu Leu Ser Thr Thr Arg Met Pro Ile Ala Thr
65                  70                  75                  80

Val Gly Arg Asn Val Gly Phe Asp Asp Gln Leu Tyr Phe Ser Arg Val
                85                  90                  95

Phe Lys Lys Cys Thr Gly Ala Ser Pro Ser Glu Phe Arg Ala Gly Cys
            100                 105                 110

Glu Glu Lys Val Asn Asp Val Ala Val Lys Leu Ser
        115                 120

<210> SEQ ID NO 5
<211> LENGTH: 17
<212> TYPE: DNA
<213> ORGANISM: Escherichia coli

<400> SEQUENCE: 5
tagcattttt atccata                                                                                17

<210> SEQ ID NO 6
<211> LENGTH: 88
<212> TYPE: PRT
<213> ORGANISM: Escherichia coli

<400> SEQUENCE: 6

Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

```
Gly Ile Arg Leu Leu Gln Glu Glu Glu Gly Leu Pro Leu Val Gly
 65                  70                  75                  80
Arg Val Ala Gly Glu Pro Leu
                85
```

<210> SEQ ID NO 7
<211> LENGTH: 40
<212> TYPE: DNA
<213> ORGANISM: Escherichia coli

<400> SEQUENCE: 7
cataaacgag cattgctgcg atatttgcag caagggagct                                40

<210> SEQ ID NO 8
<211> LENGTH: 30
<212> TYPE: DNA
<213> ORGANISM: Escherichia coli

<400> SEQUENCE: 8
aaaaccagtg aaaaccagtg aaaaccagtg                                           30

<210> SEQ ID NO 9
<211> LENGTH: 51
<212> TYPE: DNA
<213> ORGANISM: Escherichia coli

<400> SEQUENCE: 9
atatacagta ccaatataca gtaccacata tacagtacca aatatacagt a                   51

<210> SEQ ID NO 10
<211> LENGTH: 56
<212> TYPE: DNA
<213> ORGANISM: Escherichia coli

<400> SEQUENCE: 10
tactgtatat atatacagta cttatacggc aagtactact gtatatatat acagta             56

<210> SEQ ID NO 11
<211> LENGTH: 7
<212> TYPE: DNA
<213> ORGANISM: Escherichia coli

<400> SEQUENCE: 11 caaaaat                                                                    7

<210> SEQ ID NO 12
<211> LENGTH: 8
<212> TYPE: DNA
<213> ORGANISM: Escherichia coli

<400> SEQUENCE: 12 caaaaaat                                                                   8

<210> SEQ ID NO 13
<211> LENGTH: 30
<212> TYPE: DNA
<213> ORGANISM: Escherichia coli

<400> SEQUENCE: 13
atatacagta atatacagta atatacagta                                           30

<210> SEQ ID NO 14
<211> LENGTH: 30

```
<212> TYPE: DNA
<213> ORGANISM: Escherichia coli

<400> SEQUENCE: 14
atatacagta atatacagta atatacagta                          30

<210> SEQ ID NO 15
<211> LENGTH: 34
<212> TYPE: DNA
<213> ORGANISM: Escherichia coli

<400> SEQUENCE: 15
ataaaaaagc attgcttatc aatttgttgc aagg                     34
```

PROKARYOTIC TWO-HYBRID SYSTEM

CROSS-REFERENCE TO RELATED APPLICATION

This application claims the benefit of U.S. Provisional Application No. 60/032,821 filed Dec. 11, 1996.

FIELD OF THE INVENTION

This invention relates to assays for protein interactions, fusion proteins, and host cells modified to comprise such proteins.

BACKGROUND OF THE INVENTION

Homo- and heterodimeric protein complexes mediate many cellular processes and abnormal protein interactions underly various medical conditions. Yan et al. (1995) *Cancer-Res.* 55: 3569–75. Research on such complexes has led to efforts to understand disease at the molecular level and to a search for small molecule effectors of such complexes. Such effectors could modulate protein interactions and are potential therapeutic agents. Gibbs & Oliff (1994) *Cell* 79: 193–198. Most often, such effectors have been identified using various biochemical and immunological in vitro approaches. The advantages of genetic approaches in drug discovery, however, have recently received increased attention. Liuzzi et al. (1994), *Nature* 372: 695–8. These advantages include both cost-effectiveness and simplicity. Only one such genetic system, the yeast-two hybrid system, currently meets all these criteria and is also equally suitable for the detection of both homo- and heterodimeric protein interactions. Another unique feature of the yeast two-hybrid system is its ability to detect the desired protein-protein interaction without interference by competing interactions. Fields & Song (1989) *Nature* 340: 245–6. The system has been successfully used for the analysis of protein interactions and for the isolation of interacting proteins through interaction cloning. For a review, see Allen et al. (1995), *Trends in Biochem. Sci.* 20: 511–16.

Although the yeast two-hybrid system has proven highly useful, it suffers from a number of limitations. Yeast is impermeable to many small molecules, which effectively prevents their evaluation in a yeast system. Higgins (1993) *Curr. Opin. in Cell Biol.*, 5: 684–687. The yeast system also requires nuclear localization of interacting proteins, which may lead to other complications.

These problems can potentially be overcome with an *E. coli* two-hybrid system. *E. coli* strains can be hyperpermeable. Nakamura & Suganuma (1972) *J. Bacteriol.* 110: 329–35. One can use this hyperpermeability to maximize the number of small molecules that can be evaluated. In addition, *E. coli* has a rapid growth rate, permitting shorter turnaround times during drug screening. Furthermore, one can transform *E. coli* at high frequencies, facilitating interaction cloning.

To date, only one *E. coli* system seems to have properties similar to the yeast two-hybrid system, but this system has only been shown to detect homodimerization of an *E. coli* protein and there is no published evidence that the system is sufficiently robust to be useful for major two-hybrid applications such as interaction cloning. Dove et al. (1997), *Nature* 386: 627–30. Other *E. coli* systems for detecting protein interactions genetically have also been reported. Doerr et al. (1991) *Biochem.* 30: 9657–64; Marchetti et al. (1995) *J. Mol. Biol.* 248: 541–50; Jappelli & Brenner (1996) *J. Mol. Biol.* 259: 575–8. Unlike the yeast two-hybrid system, however, these systems require homodimerization of at least one of the interacting proteins and detection of the desired protein-protein interaction can be subject to interference by competing other interactions. The art would benefit from an *E. coli* two-hybrid system that can detect a variety of protein interactions and which is sufficiently robust for interaction cloning.

SUMMARY OF THE INVENTION

The present invention relates to a two-hybrid system that can detect homo- and heterodimeric protein interactions in *E. coli* and other prokaryotic cells. This system is useful for the same applications as the yeast two-hybrid system; e.g., interaction cloning, in detecting and analyzing protein interactions and detecting modulators thereof. The invention concerns a prokaryotic host cell comprising:
   (a) a fusion protein having
      (i) a first DNA-binding domain and
      (ii) a first protein-interacting domain;
   (b) a fusion protein having
      (i) a second DNA-binding domain and
      (ii) a second protein-interacting domain capable of binding to the first interacting domain; and
   (c) a nucleic acid molecule having a reporter gene operatively linked to
      (i) a promoter,
      (ii) a first operator site capable of binding to the first DNA-binding domain, located upstream of the promoter, and
      (iii) a second operator site capable of binding the second DNA-binding domain, located downstream of the promoter and the first operator site.

Binding of the first interacting domain to the second interacting domain is signaled by altered (i.e., downregulated) expression of the reporter gene. In the view of the present inventor, the fusion proteins form a loop together with the length of DNA between the binding sites. This loop apparently interferes with the activity of the RNA polymerase, perhaps by preventing its binding to the DNA.

The invention also concerns the nucleic acid molecule described in subparagraph (c) above and a vector comprising this nucleic acid molecule.

The invention further concerns a process for detecting inhibition or enhancement of binding of a first interacting domain with a second interacting domain, which comprises (a) treating a culture of cells of claim 1 with a test substance, and (b) screening for increased or decreased expression of the reporter gene, respectively.

The invention further concerns an interaction cloning method—i.e., a process for detecting a cell comprising a test domain that interact with a known domain, which comprises:
   (1) generating a library of cells in which each cell comprises:
      (a) a fusion protein having
         (i) a first DNA-binding domain and
         (ii) a known domain;
      (b) a fusion protein having
         (i) a second DNA-binding domain and
         (ii) a test domain; and
      (c) a nucleic acid molecule having a reporter gene operatively linked to
         (i) a promoter,
         (ii) a first operator site capable of binding to the first DNA-binding domain, located upstream of the promoter, and (iii) a second operator site capable of binding; the second DNA-binding domain, located downstream of the promoter and the first operator site;

(2) detecting cells exhibiting altered expression of the reporter gene, which signals interaction between the known domain and the test domain.

The invention also concerns a number of preferred variations to the above-described host cell, nucleic acid, vector, and process. The preferred first DNA-binding domain is from AraC, and the preferred first operator site is an AraC operator. The preferred second DNA-binding protein is from LexA, and the preferred second operating site is a LexA half-operator site. In another variation, the nucleic acid comprises more than one LexA operator half site. In one further preferred variation, the nucleic acid comprises a binding site for a factor such as IHF between the operator sites that causes the nucleic acid to bend upon binding. Further preferences appear in the detailed description that follows.

Although described below with *E. coli,* the invention encompasses a number of cell types. The invention may be adapted to other procaryotic cells.

BRIEF DESCRIPTION OF THE DRAWINGS

FIGS. 2A and 2B: Salient features of reporter plasmids and hybrid proteins. (A) Nucleotide sequence of the regulatory region upstream of the lacZ reporter gene in plasmid P3 (Reeder & Schleif (1993) *J. Mol. Biol.* 231: 205–218). Plasmid P3 contains an I1—I1 AraC operator and was used to construct the reporter plasmids in this study. The restriction sites for insertion of LexAOp and IHFOp are shown. −35 and −10 designate the AraC-dependent promoter that overlaps the promoter-proximal I1 site. +1 indicates the transcriptional start. See Reeder & Schleif (1993) *J. Mol. Biol.* 231: 205–218 for nucleotide sequence between HindIII and lacZ. Top strands of oligonucleotide LexAOp and IHFOp inserts are shown. Bold sequences indicate consensus LexA half sites. (B) Linear structures of hybrid proteins. Structures of wild-type AraC and LexA are shown on top. Numbers indicate boundary amino acid residues of original proteins used for hybrid construction. Dim: Dimerization domain. 'DNA' is defined in FIG. 1.

DETAILED DESCRIPTION OF THE INVENTION

Definition of Terms

Figure 1A:
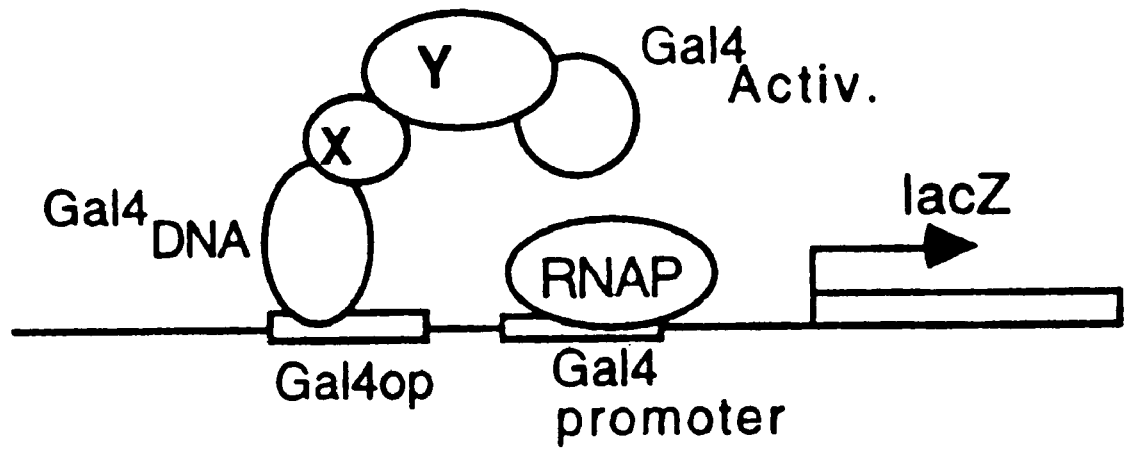
FIGS. 1A and 1B: Diagrams of gene activation. (A) Yeast two-hybrid system. (B) Proposed mechanism for a two hybrid system using hybrid operators specific for the phage P22 and 434 repressor proteins. See specification hereinafter for details. X and Y represent interacting domains used to generate hybrid proteins; Activ: Activation domain; DNA: DNA binding domain; op: operator; RNAP: RNA polymerase.

The following definitions apply to the terms as used throughout this specification, unless otherwise limited in specific instances.

The term "prokaryotic host cell" refers to such genera and species as:

*Escherichia coli*

Salmonella

Klebsiella

Pseudomonas

Caulobacter

Rhizobium and the like.

The term "first DNA-binding domain" refers to a polypeptide sequence capable of binding to an operator that could be inserted in the region upstream from the reporter gene. Such domains can retain most or all of the protein from which they are derived or merely that portion that directly participates in DNA binding. Exemplary first DNA-binding domains may be derived from AraC, its homologues such as RhaS, XylS or any other DNA binding proteins. Such proteins are described in Ramos et al. (1990) *Nucleic Acids Res.* 18: 2149.

The term "first operator site" refers to a nucleotide sequence capable of binding to the associated first DNA-binding domain. Such sequences are known in the art and can be inserted through recombinant DNA techniques.

The term "second DNA-binding domain" refers to a polypeptide sequence capable of binding to an operator that could be inserted in the region downstream from the promoter. Such domains can retain most or all of the protein from which they are derived or merely that portion that directly participates in DNA binding. Exemplary second DNA-binding domains may be derived from LexA, the phage lambda CI repressor, the repressors of phages P22 and 434, or any other DNA binding proteins that can bind DNA as fusion proteins.

The term "second operator site" refers to a nucleotide sequence capable of binding to the associated second DNA-binding domain. Such sequences are known in the art and can be inserted through recombinant DNA techniques. Exemplary sequences are LexA operator sites, including half sites thereof. The second operator site is located between the promoter and translational start site for the reporter gene, with a location between the transcriptional and translational start sites preferred.

The term "AraC binding domain" refers to a polypeptide deriveable from the AraC protein that is capable of binding to DNA. The AraC binding domain can be full-length AraC or any natural or modified fragment thereof that retains DNA binding activity. An exemplary AraC binding domain has the sequence ESLHPPMDNRVREACQYISDHLADSNF-
DIASVAQHVCLSPSR LSHLFRQQLGISV-
LSWREDQRISQAKLLLSTTRMPIATVGRN VGFD-
DQLYFSRVFKKCTGASPSEFRAGCEEKVNDVAV
KLS (SEQ ID NO: 4).

The term "AraC operator site" refers to a nucleotide sequence capable of binding to AraC. Exemplary nucleotide sequences include

TAGCATTTTTATCCATA (SEQ ID NO: 5).

The term "LexA binding domain" refers to a polypeptide deriveable from LexA that is capable of binding to DNA. The LexA binding domain can be full-length LexA or any natural or modified fragment thereof that retains DNA binding activity. An exemplary LexA binding domain has the sequence MKALTARQQEVFDLIRDHISQTGMPP-
TRAEIAQRLGFRSPNAA EEHLKALARKGVIE-
IVSGASRGIRLLQEEEEGLPLVGRVAAGEPL (SEQ
ID NO: 6).

The term "LexA operator site" refers to a nucleotide sequence capable of binding to LexA. LexA operators may be one or more consensus and/or nonconsensus half-sites, which may or may not be oriented as inverted repeats. Exemplary nucleotide sequences include LexA operator half sites, which can conform to the consensus sequence

TACTGTATAT (SEQ ID NO: 2).

Exemplary LexA operators include:

LexA colE1 operator half site as triple direct repeats:
5'-AAAACCAGTGAAAACCAGTGAAAACCAGT
G-3' (SEQ ID NO: 8)

LexA consensus half sites as quadruple direct repeats with 3 or 4 bp spacers shown in bold:
5'-ATATACAGTACCAATATACAGTACC
ACATATACAGTACCAAATATACAGTA-3' (SEQ
ID NO: 9)

Two full-length consensus LexA sites with 16 bp spacer shown in bold:
5'-TACTGTATATATACAGTACTTATACG
GCAAGTACTACTGTATATATATACAGTA-3' (SEQ
ID NO: 10)

The term "reporter gene" refers to any gene whose expression provides a measurable signal. Exemplary reporter genes include the genes for β-galactosidase, antibiotic resistance genes (e.g., chloramphenicol transferase), and toxic genes (e.g., GATA-1 DNA binding domains, colicin lysis genes, and the like). Various other reporter genes are well known by those having ordinary skill in the art.

The phrase "factors capable of causing the nucleic acid molecule to bend between the first and second operator sites" refers to any of a number of proteins that bind DNA and cause deformation of the linear axis of the helix. Exemplary factors are IHF, TF1, HU, CAP or intrinsically bent DNA sequences such as $C(A)_{5-6}T$ (i.e., CAAAAAT (SEQ ID NO:11) and CAAAAAAT (SEQ ID NO: 12)), and the like. Geidschek et al. (1990) *J. Struc. Biol.* 104: 84–90; Hodges-Garcia et al. (1989) *J. Biol. Chem.* 264: 14621–3; Wu & Cruthers (1984) *Nature* 308: 509–13; Kahn & Crothers (1992) *Proc. Natl. Acad. Sci. U.S.A.* 89: 634307; Goodman et al. (1989) *Nature* 341: 244–51; Goodman et al.. (1992), *Proc. Natl. Acad. Sci.* 89:11910–14. The associated binding site may be any nucleotide sequence capable of such binding (e.g., the consensus binding site for IHF, the nucleotide sequence of SEQ ID NO: 3)

$TX_6ATXAX_2TX_2AXTXAAATCAAXAAGTTAX_6A$
SEQ ID NO: 3.

Process of preparation

Gene constructs

The nucleic acids used in the present invention may be prepared by recombinant nucleic acid methods. See, for example, the recombinant DNA methods of Nelles et al. (1987), *J. Biol. Chem.* 262: 10855. Exemplary strains comprising such constructs areas described in the figure legends.

The DNA sequences may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for the desired activity.

For cDNA, the cDNA may be cloned and the resulting clone screened with a probe for cDNA coding for the desired region. Upon isolation of the desired clone, the cDNA may be manipulated in substantially the same manner as the genomic DNA.

To express the DNA sequences, transcriptional and translational signals recognized by an appropriate host are necessary. Alternatively, the promoter region from genomic DNA may be obtained in association with the DNA sequence for the fusion protein. To the extent that the host cells recognize the transcriptional regulatory and translational initiation signals associated with the fusion protein, the 5' region adjacent to the coding sequence may be retained and employed for transcriptional and translational regulation. This region typically will include those sequences involved with initiation of transcription and translation, such as the TATA box, capping sequence, CAAT sequence, and the like. Typically, this region will be at least about 150 base pairs long, more typically about 200 bp, and rarely exceeding about 1 to 2 kb.

The non-coding 3' region may be retained, as well, especially for its transcriptional termination regulatory sequences, such as the stop signal and polyadenylated region. In addition, the non-coding 3' region may also contain an enhancer. Where the transcriptional termination signals are not satisfactorily functional in the host cell, then a functional 3' region from a different gene may be substituted. In this method, the choice of the substituted 3' region would depend upon the cell system chosen for expression.

A wide variety of transcriptional and translational regulatory sequences may be employed, depending upon the nature of the host. The transcriptional and translational regulatory sequences may be derived from viral sources (e.g., adenovirus, bovine papilloma virus, Simian virus, and the like) where the regulatory signals are derived from a gene that has a high level of expression in the host. Alternatively, promoters from mammalian expression products (e.g., actin, collagen, myosin, and the like) may be employed. Transcriptional initiation regulatory signals may be selected that allow for repression or activation, so that expression of the genes can be modulated. One such controllable modulation technique is the use of regulatory signals that are temperature-sensitive, so that expression can be repressed or initiated by changing the temperature. Another controllable modulation technique is the use of regulatory signals that are sensitive to certain chemicals.

To form the reporter or DNA binding domain-interacting, domain chimeric gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments.

The construct for a DNA binding domain-interacting domain (e.g., for AraC or LexA and their respective fusion partners) may be joined together to form a single DNA segment or may be maintained as separate segments by themselves or in conjunction with vectors. The constructs may be introduced into a cell by transformation in conjunction with a gene allowing for selection where the construct will become integrated into the host genome. Usually, the construct will be part of a vector having a replication system recognized by the host cell.

Expression vectors

Expression vehicles for production of the molecules of the invention include plasmids or other vectors. In general, such vectors contain control sequences that allow expression in various types of hosts, including prokaryotes. Suitable expression vectors containing the desired coding and control sequences may be constructed using standard recombinant DNA techniques known in the art, many of which are described in Sambrook et al. (1989), *Molecular Cloning: A Laboratory Manual,* Second Edition, Cold Spring Harbor Laboratory, Cold Spring Habor, N.Y.

An expression vector as contemplated by the present invention is at least capable of directing the replication of the reporter gene construct and the replication and expression of the DNA binding domain-interacting domain construct. One class of vectors utilizes DNA elements that provide autonomously replicating extrachromosomal plasmids derived from animal viruses (e.g., bovine papilloma virus, polyomavirus, adenovirus, or SV40). A second class of vectors relies upon the integration of the desired gene sequences into the host cell chromosome.

Expression vectors useful in the present invention typically contain an origin of replication, a promoter located 5' to (i.e., upstream of) the DNA sequence to be expressed, and a transcription termination sequence. Suitable origins of replication include, for example, the ColE1, pSC101, SV4O and M13 origins of replication. Suitable termination sequences include, for example, the bovine growth hormone, SV40, lacZ and AcMNPV polyhedral polyadenylation signals. Suitable promoters include, for example, the cytomegalovirus promoter, the lacZ promoter, the gal 10 promoter and the AcMNPV polyhedral promoter. The promoter sequence may also be inducible, to allow modulation of expression (e.g., by the presence or absence of nutrients or other inducers in the growth medium). One example is the lac operon obtained from bacteriophage lambda plac5, which can be induced by IPTG.

The expression vectors may also include other regulatory sequences for optimal expression of the desired product. Such sequences include stability leader sequences, which provide for stability of the expression product; secretory leader sequences, which provide for secretion of the expression product; enhancers, which upregulate the expression of the DNA sequence; and restriction enzyme recognition sequences, which provide sites for cleavage by restriction endonucleases. All of these materials are known in the art and are commercially available. See, for example, Okayama (1983), *Mol. Cell. Biol.,* 3: 280.

A suitable expression vector may also include marking sequences, which allow phenotypic selection of transformed host cells. Such a marker may provide prototrophy to an auxotrophic host, biocide resistance (e.g., antibiotic resistance) and the like. The selectable marker gene car either be directly linked to the DNA gene sequences to be expressed, or introduced into the same cell by co-transfection. Examples of selectable markers include neomycin, ampicillin, hygromycin resistance and the like.

The characteristics of the actual expression vector used must be compatible with the host cell that is to be employed. Suitable commercially available expression vectors into which the DNA sequences of the present invention may be inserted include pSPORT, pBluescriptIISK, the baculovirus expression vector pBlueBac, and the prokaryotic expression vector pcDNAII, all of which may be obtained from Invitrogen Corp., San Diego, Calif.

Host cells

The present invention additionally concerns hosts for the chimeric gene constructs and reporter plasmids. Suitable host cells include prokaryotic cells in which endogenous activities do not interfere with the function of the two-hybrid system. Such *E. coli* strains include MC1061, DH5a, Y1090 and JM101.

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed. Host cells containing an expression vector may be identified by any of a number of methods known in the art.

DETAILED DESCRIPTION OF PREFERRED EMBODIMENTS

Below are detailed descriptions of specific embodiments of the present invention. These embodiments are exemplary and serve to illustrate the broad applicability of the present invention.

The yeast two-hybrid system is a powerful genetic tool for detecting and analyzing homo- and heterodimeric protein interactions. Here we describe a mechanistically different *E. coli* two-hybrid system where protein interaction represses reporter gene activity. The system employs hybrids of two *E. coli* proteins, the activator protein AraC and the repressor protein LexA. AraC hybrids alone activate a lacZ reporter gene from a high affinity operator directly upstream of the araBAD promoter that controls lacZ. LexA hybrids can repress this activation by up to 50-fold, but only if the hybrids have cognate interaction modules and the reporter plasmid contains LexA operator site(s) several helical turns downstream of the promoter in the 5' untranslated leader of lacZ. These requirements suggest that repression occurs because DNA looping between operator-bound heterodimeric hybrids excludes RNA polymerase from the lacZ promoter inside the loop. Consistent with a mechanism based on DNA looping, repression is enhanced with the *E. coli* DNA bending protein IHF bound between the operators. The results described here, suggest that the *E. coli* two-hybrid system will permit highly efficient interaction cloning and promises to be particularly useful for drug discovery and the analysis of interactions between bacterial proteins.

MATERIALS AND METHODS

Standard cloning and immunoblotting techniques were used. Sambrook et al. (1989), *Molecular Cloning: A Laboratory Manual,* Second Edition, Cold Spring Harbor Laboratory, Cold Spring Habor, N.Y.). Miller units of LacZ activity were calculated from a time course of 9 readings/ sample on a BioTekTM EL-340 96-well microplate reader at 30° C. and with Chlorophenolred-b-D-galactopyranoside (CPRG; Boehringer Mannheim) as a substrate. Miller (1972) *Experiments in molecular genetics.* Cold Spring Harbor Laboratory, Cold Spring Harbor, N.Y.; Menzel (1989) *Anal. Biochem.* 181, 40–50. For assays, *E. coli* MC1061 containing expression- and/or reporter plasmids was grown for at least 7 generations in LB-broth in microtiter plates in the presence of inducer (IPTG, Fisher Biotech; anhydrotetracycline, Acros) at 37° C. to A600=0.2–0.4. Meissner et al. (1987) *Proc. Natl. Acad. Sci. U.S.A.* 84, 4171–4175. Under these conditions, LacZ activities are generally about 5-fold lower than reported previously. Bustos & Schleif (1993), *Proc. Natl. Acad. Sci. U.S.A* 90: 5638–42; Reeder, T. & Schleif, R. (1993) *J. Mol. Biol.* 231, 205–218. HimD::cat was tested in strain TR321 after phage P1 transduction from strain HN1069. Bustos & Schleif (1993), *Proc. Natl. Acad. Sci. U.S.A.* 90: 5638–42; Flamm, E. L. & Weisberg, R. A. (1985) *J. Mol. Biol.* 183, 117–128.

Reporter plasmids are based on plasmid P3 (ColE1, Amp$^r$) (FIG. 2A; 11) or pMS421 (pSC101, Spec$^r$). Churchward, G., Belin, D. & Nagamine, Y. (1984) *Gene* 31, 165–171. LexA and IHF sites (FIG. 2A) are oligonucleotide inserts where the mutant IHF site is in:

5'-CATAAACGAGCATTGCTGCGATATTTGCAGC AAGGGAGCT-3' (SEQ ID NO: 7).

Figure 2B:
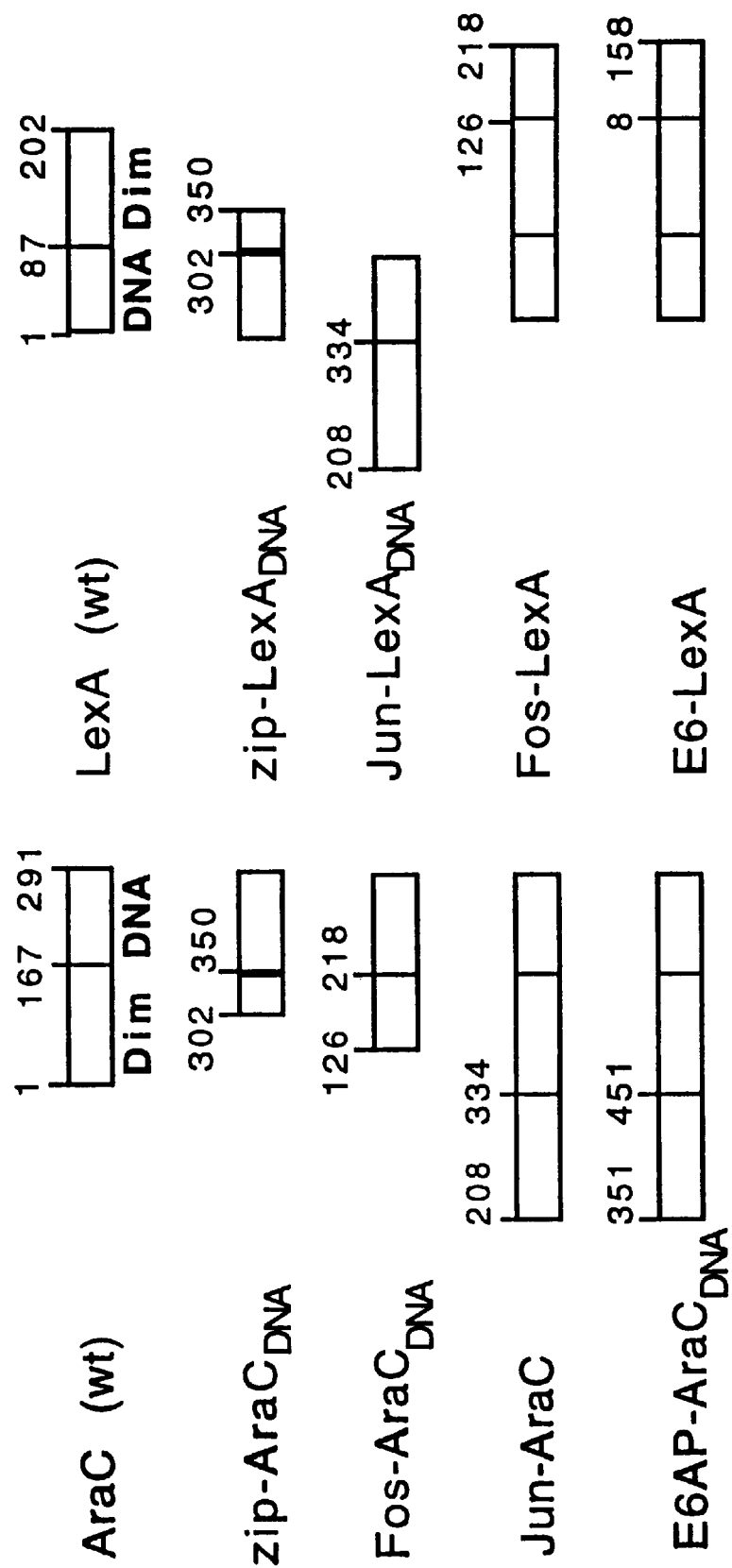

See FIG. 2B for structures of hybrid proteins. araC constructs are under the IPTG-inducible pSE380 trp/lac promoter on p15A replicons (Cm$^r$ or Km$^r$; Invitrogen. Bustos & Schleif (1993), *Proc. Natl. Acad. Sci. U.S.A.* 90: 5638–42. LexA$_{DNA}$ constructs are under a second pSE380 regulatory element downstream and in tandem with the araC construct. Assays involving LexA$_{DNA}$ were in strains with pP3-based reporter plasmids, p15A-based hybrid constructs and pMS421 which carries lacI$^q$. For assays with hybrids; of full-length LexA, reporter constructs were on pMS421 and lexA constructs under the anhydrotetracycline-inducible tet promoter in pASK75 (ColE1, Amp$^r$. Skerra, A. (1994) *Gene* 151, 131–135. Zip-AraC$_{DNA}$, zip-LexA$_{DNA}$, AraC$_{DNA}$ and AraC are from pGB009, pGB004, pGB021b and pGB020, respectively. Bustos & Schleif (1993), *Proc. Natl. Acad. Sci. U.S.A.* 90: 5638–42. Mouse c-fos and c-jun contain residues 126–218 and residues 208–324, respectively. Kouzarides, T. & Ziff, E. (1989) *Nature* 340, 568–571. See Ryseck, R. P., Kovary, K. & Bravo, R. (1990) *Oncogene* 5, 1091–1093 for Fos mutation IVM54. E6 and E6AP domains are residues 8–158 and 351–451, respectively. Huibregtse, J. M., Scheffner, M. & Howley, P. (1991) *EMBO J.* 10, 4129–4135.

RESULTS

Activation of a lac reporter gene by heterodimeric *E. coli* AraC and LexA hybrid proteins in an *E. coli* two-hybrid system.

Figure 1B:
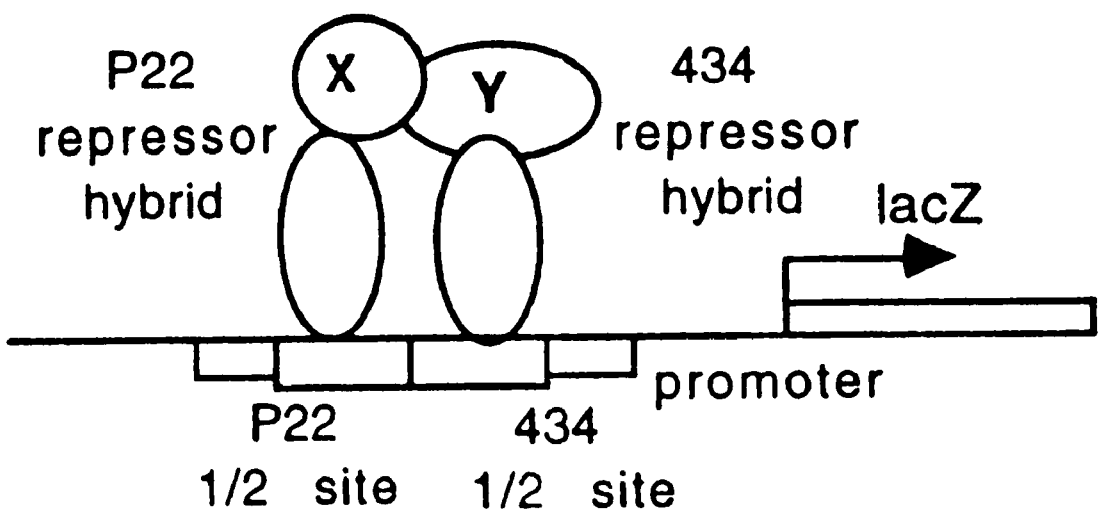

Ptashne and coworkers described a general approach towards a bacterial two-hybrid system, using as models the repressor proteins of bacteriophages P22 and 434. Hollis et al. (1988), *Proc. Natl. Acad. Sci. U.S.A.* 85: 5834–8. These repressors only bind their operators as dimers and they can heterodimerize, but they do not recognize each others operators. However, heterodimers can act as repressors with hybrid operators where each half site is specific for one of the repressors (FIG. 1B). These results suggested a two-hybrid system where repression from a hybrid operator would indicate interaction of other proteins when they replace the dimerization domains of the phage P22 and 434 repressors.

We chose the *E. coli* AraC and LexA proteins for a similar activation-approach in an *E. coli* two-hybrid system. AraC is a transcriptional activator that binds as a dimer to an operator of two tandem half sites, I1 and I2, just upstream of the AraC dependent araBAD promoter (FIG. 1B). Schleif (1996) in *Escherichia coli and Salmonella typhimurium. Cellular and Molecular Biology,* (Neidhardt, ed.), ASM Press, Washington, D. C., 1300-9. LexA is a transcriptional repressor which cooperatively binds as a dimer to an operator of two inverted half sites. LexA has been used to provide the DNA binding function in the yeast two-hybrid system. Allen et al. (1995), *Trends in Biochem. Sci.* 20: 511–6. Both AraC and LexA have dimerization domains that can be functionally replaced by self-associating foreign proteins, such as the c/EBP leucine zipper (zip) to generate zip-AraC$_{DNA}$ and zip-LexA$_{DNA}$ hybrids. Bustos & Schleif (1993), *Proc. Natl. Acad. Sci. U.S.A.* 90: 5638–42.

Several lines of indirect evidence suggest that the AraC-RNA polymerase contacts necessary for activation of araBAD may only require the promoter-proximal subunit of the dimer present at the low affinity I2 half site. Schleif (1996) in *Escherichia coli and Salmonella typhimurium. Cellular and Molecular Biology,* (Neidhardt, ed.), ASM Press, Washington, D. C., 1300-9. I2 is accessed cooperatively when the other dimer subunit is bound at the promoter-distal high affinity I1 site. We reasoned that zip-AraC$_{DNA}$/zip-LexA$_{DNA}$ heterodimers might activate araBAD from a hybrid operator when a LexA half-site (LexAOp) replaces the AraC I1 site (see FIG. 2 for araBAD-lac reporter plasmid and structures of hybrids). Although each hybrid can homodimerize, the LexA hybrid homodimer, however, should be unable to bind to the hybrid LexAOp-I2 operator because its cooperative binding requires two LexA half sites. Bustos & Schleif (1993), *Proc. Natl. Acad. Sci. U.S.A.* 90: 5638–42; Kim & Little (1992) *Science* 255: 203–6. Likewise, AraC hybrid homodimers should be unable to bind the hybrid operator because the low-affinity I2 half site does not bind AraC on its own. Reeder, T. & Schleif, R. (1993) *J. Mol. Biol.* 231, 205–218. Thus, activation would reflect heterodimerization of the hybrids through their zip domains, followed by cooperative binding of the heterodimer to the LexAOp-I2 hybrid operator. This approach was unsuccessful despite many attempts to optimize DNA binding of the heterodimers (e.g. spacings of 4, 11 or 22 bp between the operator half sites). In some instances, a low level of activation of the lac gene by the AraC hybrid alone was in fact marginally repressed upon coexpression of an interacting LexA hybrid, which indicated to us that the heterodimer subunits may actually interfere with each others binding to the closely spaced operator half sites. We also made various attempts at replacing zip-LexA$_{DNA}$ and its site with a zip-RhaS$_{DNA}$ hybrid and RhaS operator half site, again without success. RhaS is a close structural and functional homologue of AraC; see Ramos et al. (1990) *Nucleic Acids Res.* 18: 2149–52. The results suggest that an AraC monomer at I2 may not be sufficient for activation of the araBAD promoter.

Repression of an activated lac reporter gene by heterodimeric *E. coli* AraC and LexA hybrid proteins in an *E. coli* two-hybrid system.

Figure 3A:
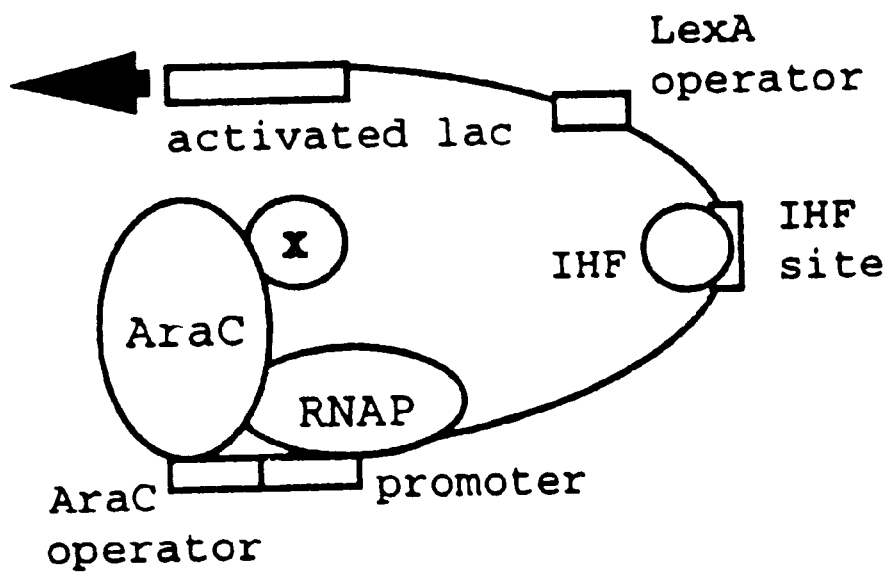
FIGS. 3A and 3B: Diagram outlining the mechanism of this *E. coli* two-hybrid system. See text for details.
Figure 3B:
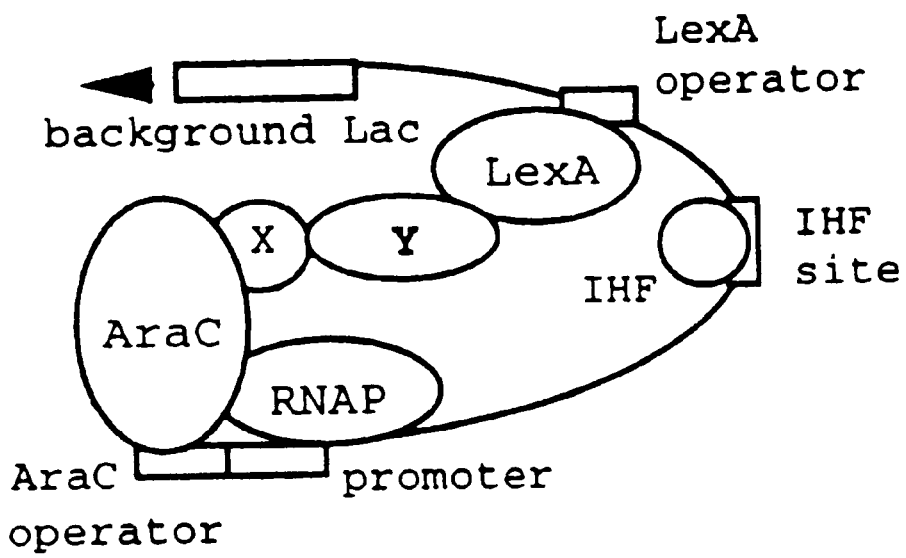

As a new approach, we decided to set up a repression system where an initial activation event by AraC hybrids would be inhibited after an interacting LexA hybrid binds at LexAOp. As an AraC operator, we used the high affinity I1—I1 site which can bind dimeric and monomeric AraC molecules such as wild-type AraC and AraC$_{DNA}$, respectively. (FIG. 2A; Bustos & Schleif (1993), *Proc. Natl. Acad. Sci. U.S.A.* 90: 5638–42; Reeder, T. & Schleif, R. (1993) *J. Mol. Biol.* 231, 205–218. Since I1—I1 can also mediate activation of araBAD-lac by those dimeric and monomeric AraC molecules (Bustos & Schleif (1993), *Proc. Natl. Acad. Sci. U.S.A.* 90), we reasoned that this would allow us to examine hybrid interactions even if the fusion partner of $AraC_{DNA}$ fails to self-associate. Since the activation-based approach towards our *E. coli* two-hybrid system may have failed because the zip-$Arac_{DNA}$ and zip-$LexA_{DNA}$ heterodimer subunits may be unable to simultaneously bind closely spaced LexAOp and AraC operator sites (see above), we increased the spacing of the AraC and LexA operators by placing LexAOp several helical turns or at least 50 bp downstream of the promoter within the 5' untranslated leader of the lacZ reporter gene (FIG. 2A). We hoped that zip-$AraC_{DNA}$ hybrids bound at the I1—I1 operator would mediate cooperative binding of zip-$LexA_{DNA}$ at LexAOp in an interaction-dependent manner. Operator binding of the LexA hybrid would presumably require looping of the DNA between the operators so that the operator sites are sufficiently close to each other for simultaneous binding of the heterodimer subunits. Finally, the approach assumes that twisting of the DNA between the operators would help to position the operators relative to each other for optimal access by the heterodimer subunits (FIG. 3). Presumably, the operator-bound LexA hybrid interferes with activation by blocking the progression of RNAP (Elledge & Davis (1989), *Genes & Dev.* 3: 185–197), by excluding it from the promoter inside the DNA loop, (FIG. 3; See Mueller et al. (1996), *J. Mol. Biol.* 257: 21–9; Choy & Adhya (1992), *Proc. Natl. Acad. Sci. U.S.A.* 89: 11264–8; Huo et al. (1988), *Proc. Natl. Acad. Sci. U.S.A.* 85: 5444–8), or by sterically interfering with the AraC-RNAP contacts.

We inserted three tandem copies of LexAOp into either the XbaI or HindIII sites in the 5' untranslated leader of the lacZ gene on the reporter plasmid (FIG. 2A). We also inserted the lambda H' site (IHFOp; Yang & Nash (1994), *Proc. Natl. Acad. Sci.* 91: 12183–12187) for the *E. coli* IHF protein into the SacI site between I1—I1 and LexAOp (FIGS. 2A and 3). Since IHF enhances DNA looping by bending DNA (Nash (1990) *Trends Biochem. Sci.* 15: 222–7. Pratt et al. (1996) *Mol. Microbiol.* 20: 911–7; Hoover et al (1990) *Cell* 63: 11–22), we hoped that IHF-mediated DNA looping in our system would enhance repression.

Homo- and heterodimeric protein interactions can mediate repression.

We have tested our general scheme with both a zip-$AraC_{DNA}$/zip-$LexA_{DNA}$ hybrid pair, and a second set of hybrids in which the interaction domains of Fos and Jun were fused to $AraC_{DNA}$ and $LexA_{DNA}$, respectively (FIG. 2B). Unlike the c/EBP zip domain, Fos does not self-associate. Halazonetis et al. (1988) *Cell* 55: 917–24. Repression with the hybrid pair would provide direct evidence that the oligomerization state of AraC hybrids is not important for repression or the initial activation event at I1—I1. The interaction domain of Jun can mediate dimerization when fused to $LexA_{DNA}$ and the Fos domain can disrupt Jun-$LexA_{DNA}$ dimers in vitro. Doerr et al. (1991) *Biochem.* 30: 9657–64.

Figure 4A:
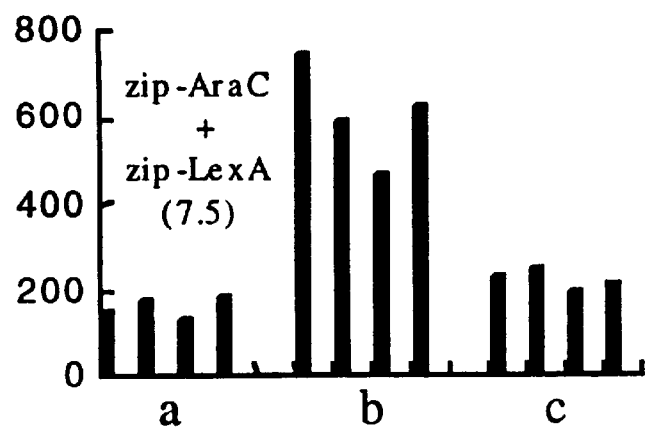
FIGS. 4A through 4F: Original assay results. (A–E) with reporter plasmid P3IHFLexAOpX; (F) with reporter plasmid P3IHFLexAOpmH. a: reporter strain alone; b: reporter strain with AraC construct; c: reporter strain with AraC and LexA constructs. Hybrid pairs are indicated and repression ratios are given in brackets. AraC and LexA refer to the DNA binding domains of these proteins, AraC(wt) is wild-type AraC, mFos is Fos with the IVM54 mutation. Four colonies of each strain were assayed (Materials & Methods) and average activities were used to calculate repression ratios (see text). Where tested, repression ratios did not significantly change when assaying more than four colonies. Vertical axis indicate LacZ activities as Miller units.
Figure 4B:
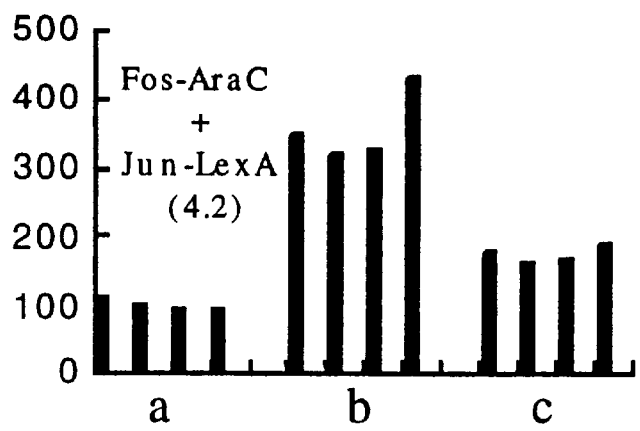

We are able to most clearly demonstrate repression in our LexA-AraC system when we use the zip-$LexA_{DNA}$/zip-$AraC_{DNA}$ hybrid pair with a reporter plasmid that contains IHFOp inserted at SacI and LexAOp at XbaI (P3IHFLexAOpX). In FIG. 4A, we note that this reporter plasmid expresses 160 units of β-galactosidase when present alone. This basal level of expression is substantially above the approximately 40 units of activity noted with the reporter plasmid in the absence of LexOp. See table 3 below and Reeder and Schleif (1993), *J. Mol. Biol.* 231: 205–218. We believe that the enhanced expression represents a contribution made by the fortuitous promoter(s) introduced with the LexOp sites (see below). The basal level of expression is elevated to 620 units in the presence of zip-$AraC_{DNA}$. In the presence of both zip-$LexA_{DNA}$ and zip-$AraC_{DNA}$, expression drops to 220 units demonstrating repression. If we subtract the basal level of expression (160 units) from that noted with zip-$AraC_{DNA}$ (620 units), we obtain a value of 460 units which we believe represents the expression resulting from the activation of the AraC-controlled promoter. Likewise, when the basal level is subtracted from the expression seen when zip-$LexA_{DNA}$ and zip-$AraC_{DNA}$ are coexpressed, we obtain a value which represents the reduced residual activation noted with the interacting pair (60 units). We define the ratio of these two values as the repression factor; 460/60=7.5 in this case. In FIG. 4B, we show that repression is also be seen with another interacting fusion pair, Jun-$LexA_{DNA}$ and Fos-$AraC_{DNA}$. In this instance a repression factor of 4.2 is noted. We will demonstate below that optimal repression requires interacting protein domains in the chimera, appropriately positioned DNA binding sites, and IHF with its appropriate binding site.

IHF can enhance repression.

We can show that IHF is involved in repression by noting reduced repression when IHF is removed by mutation or by deletion of the IHF binding site. In Table 1 we see that repression with both the Fos-$AraC_{DNA}$/Jun-$LexA_{DNA}$ and zip-$AraC_{DNA}$/zip-$LexA_{DNA}$ hybrid pairs is reduced by a factor of 2 with a reporter construct that contains LexAOp at the XbaI site, but lack IHFOp at the SacI site (P3LexAOpX vs P3IHFLexAOpX). Surprisingly, when LexOp site is placed at the HindIII site, the presence of IHFOp site is without an effect (Table 1; P3LexAOpH vs P3IHFLexAOpH). Apparently the ability of IHF to facilitate repression is dependent on the detailed geometry of our putative repression loop; its aids in repression with the small 117 bp loop when LexAOp is at XbaI, but is without effect with the larger 180 bp loop that is formed with LexAOp at HindIII.

Figure 4C:
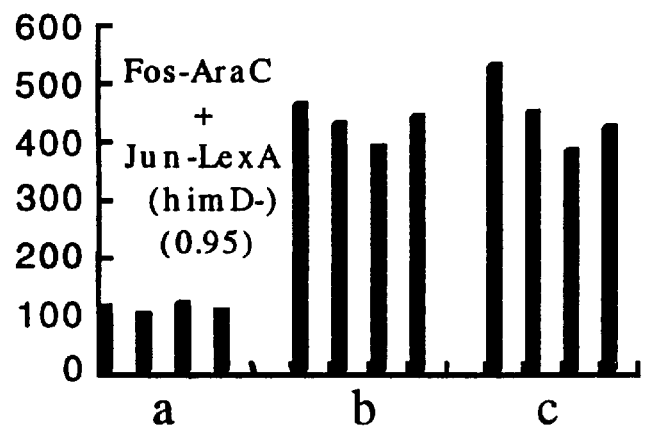

The IHFOp oligonucleotide insert has a length of 40 bp. This corresponds to roughly 3.6 turns of the helix (FIG. 2A; Lee & Schleif (1989), *Proc. Natl. Acad. Sci.* 86: 476–480), which raised the possibility that IHFOp enhanced repression with P3LexAOpX because of altered relative positioning of the interacting hybrids on the face of the helix. When we mutated the bases comprising the consensus IHF binding site while maintaining the length of IHFOp (Materials & Methods), repression with both hybrid pairs :s reduced to values similar to those seen without the IHFOp insert. Furthermore, we are able to show that repression with the Fos-$AraC_{DNA}$/Jun-$LexA_{DNA}$ and P3IHFLexAOpX is completely eliminated in a strain carrying the chromosomal himD::cat mutation which inactivates the HimD subunit of IHF (compare FIGS. 4B and 4C).

Based on these results, optimal repression with P3LexAOpX therefore occurs when an IHFOp site is present at SacI and the strain is himD$^+$. Removal of IHFOp reduces repression with zip-$AraC_{DNA}$/zip-$LexA_{DNA}$ and this same manipulation or removal of HimD by mutation completely eliminate repression with Fos-$AraC_{DNA}$/Jun-$LexA_{DNA}$ (see below for details). We believe that the enhancement of repression by IHF is the result of DNA loop formation which aids in bringing the AraC and LexA operator sites into spatial proximity for enhanced binding by heterodimeric hybrids.

Repression requires hybrid interaction.

Figure 4D:
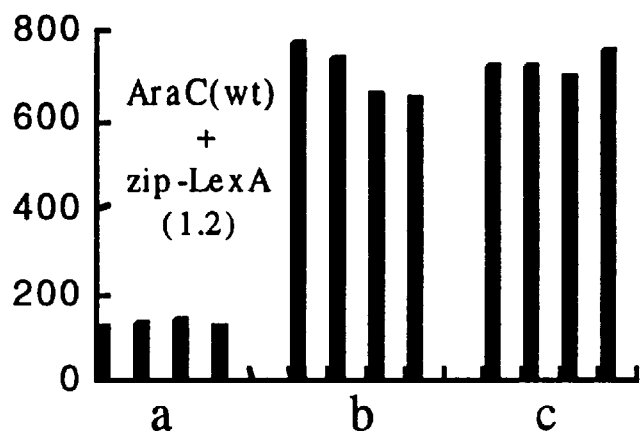
Figure 4E:
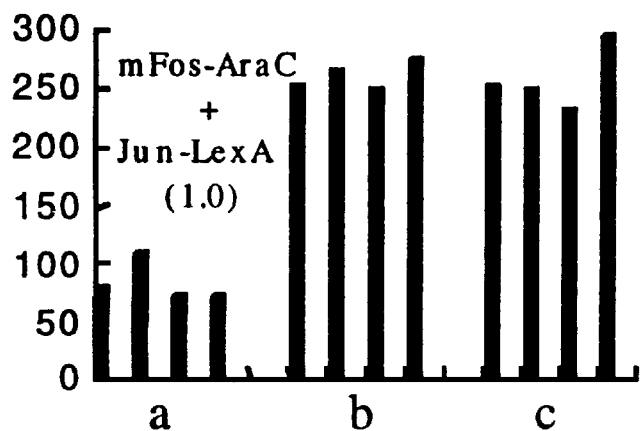
Figure 4F:
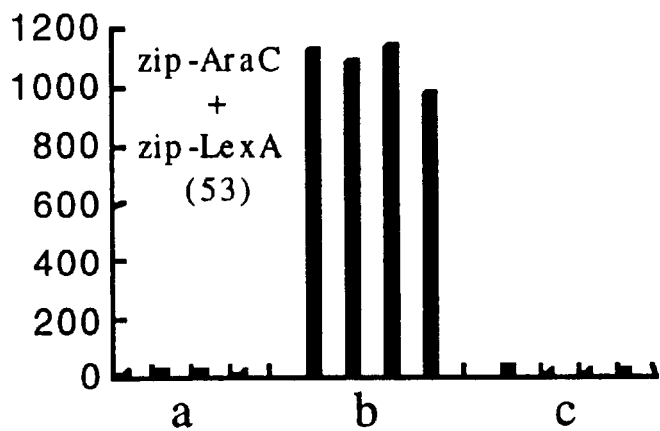

Full repression is only noted when the fused domains of the chimeric protein partners are able to interact, as in our examples with the zip and Jun/Fos pairs (FIG. 4A and Table I). When noninteracting pairs are present, repression is not detectable (e.g. when wild type AraC or AraC$_{DNA}$ are paired with zip-LexA$_{DNA}$ or when AraC$_{DNA}$ is paired with Jun-LexA$_{DNA}$; FIG. 4D and Table 2). Repression is also absent when normally interacting protein partners (Jun/Fos) have their interaction disrupted by the introduction of a specific mutation, as in our example with the Fos IVM54 point mutation (FIG. 4E) which has been previously shown to block Fos/Jun heterodimerization. Ryseck et al. (1990), *Oncogene* 5: 1091–3. Western blot analysis has not given any indications that the differences in repression levels noted with the various reporter construct and hybrid pairs can be contributed to altered hybrid protein levels; the repression described above therefore does not simply reflect altered relative amounts of the AraC and LexA proteins.

Reducing background Lac reporter activity improves repression.

Table 3A shows that the reporter plasmids of this study produce close to 10-fold higher background (AraC-independent) lac transcription than the parent plasmid P3. Inspection of the LexAOp sequence revealed that each LexA half site contains a putative −10 *E. coli* promoter sequence (FIG. 2; 5'-TACAGT-3') that might act with upstream −35 promoter-like sequences to promote AraC independent lac transcription. We changed the putative −10 sequences of P3IHFLexAOpH to 5'-ACCAGT-3' to eliminate −10 activity while leaving intact the CAG trinucleotide that constitutes the core consensus LexA binding site. Lewis et al. (1994), *J. Mol. Biol.* 241: 507–523. The manipulation decreased background Lac activity by about 20-fold (290 Miller units of Lac activity are reduced to about 17 Miller units). To demonstrate that the new reporter plasmid (P3IHFLexOp$_m$H) permits increased repression, we assayed repression with the zip-AraC$_{DNA}$/zip-LexA$_{DNA}$ interacting pair. We observe improved repression: the 5-fold repression with P3IHFLexAOpH (Table 1) increases to about 50-fold with P3IHFLexAOp$_m$H (Table 3B and FIG. 4). Repression remained negligible with the non-interacting AraC$_{DNA}$/Jun-LexA$_{DNA}$, AraC$_{DNA}$/zip-LexA$_{DNA}$ and AraC/zip-LexA$_{DNA}$ hybrid pairs (Table 3B).

Zip-AraC$_{DNA}$ and wild-type AraC generate about 1000 Miller units of Lac activity with P3IHFLexAOp$_m$H plasmid. This 60-fold activation of lac above background compares favourably with the approximately 100-fold activation reported for the parent plasmid P3. Reeder & Schleif (1993), *J. Mol. Biol.* 231: 205–218. Therefore, the low activation seen with the unmodified reporter plasmids reflects interference by the high background of AraC-independent Lac activity associated with these plasmids. As demonstrated with P3IHFLexAOp$_m$H, this problem can be eliminated by reducing AraC-independent background lac transcription.

An improved two-hybrid system.

The affinity for LexA of the nonconsensus LexA site in LexAOpm is unknown, but it is predicted to be less than the affinity of LexAOp. Lewis et al. (1994), *J. Mol. Biol.* 241: 507–523. LexAOpm improves repression with zip-AraC$_{DNA}$/zip-LeXA$_{DNA}$ (see above), but almost completely abolishes repression by Fos-AraC$_{DNA}$/Jun-LexA$_{DNA}$ (not shown). These results most likely reflect the fact that foreign fusion domains can alter the operator affinity of LexA$_{DNA}$ (Golemis & Brent (1992) *Mol. Cell. Biol.* 12: 3006–3014) and they suggest that Jun-LexA$_{DNA}$ has a lower affinity for LexA operators than zip-LexA$_{DNA}$.

These observations suggest that repression in our system can generally be maximized by improving the affinity of LexA operators. Reversal of the AraC and LexA fusion partners or fusions to the C-terminus of wild-type LexA may also minimize inhibitory effects of the fusion domain on LexA$_{DNA}$. Golemis & Brent (1992) *Mol. Cell. Biol.* 12: 3006–14. High affinity LexA operators with low endogenous promoter activity should minimize interference of background lac activity with the repression signal. Repression, may also be enhanced by overexpressing LexA hybrids. Finally, AraC$_{DNA}$ activates less efficiently than full-length AraC. Bustos & Schleif (1993) *Proc. Natl. Acad. Sci. U.S.A.* 90: 5638–42. Hybrids of full-length AraC may therefore improve repression by providing a greater activation signal.

Figure 5:
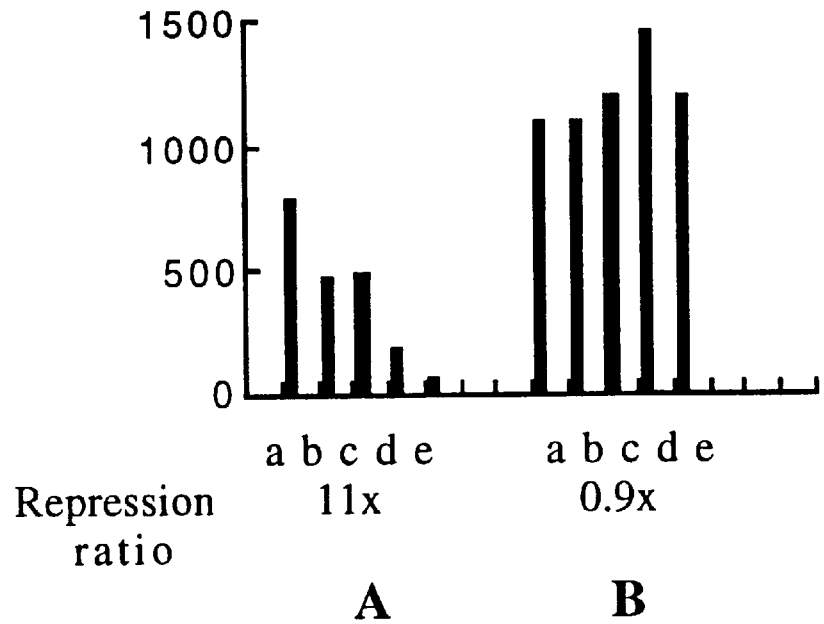
FIG. 5: Dependence of repression on intracellular levels of LexA hybrids. (A) Jun-AraC/Fos-LexA. (B) Non-interacting control hybrid pair AraC/Fos-LexA. Aliquots of a diluted preculture of each strain were grown with IPTG and anhydrotetracycline (AT) to induce expression of AraC and LexA constructs, respectively. IPTG was used at 1 mM. The amount of LexA hybrid was titrated with the following amounts of AT (ng/ml): a: 160, b: 120, c: 80, d: 40, e: 0. Maximum repression ratios are indicated.

To test if manipulation of these parameters improves repression with the Fos/Jun interaction pair, we generated reporter plasmid P3IHFLexAOpimpX by replacing LexAOpmX with three tandem direct repeat impAB LexA operator half sites which are known to have a high affinity for LexA (Lewis et al. (1994), *J. Mol. Biol.* 241: 507–523) and a low endogenous promoter activity of approximately 10 Miller units. We also fused Jun to full-length AraC and Fos to the C-terminus of full-length LexA expressed from the strongly anhydrotetracycline-inducible tet promoter (see Materials & Methods) to generate the Jun-AraC/Fos-LexA hybrid pair in FIG. 2B (see Materials & Methods). We observe a repression ratio of about 11-fold. This constitutes a three-fold improved level of repression when compared with our results for the Fos-AraC$_{DNA}$/Jun-LexA$_{DNA}$ hybrid pair (compare Table 1 and FIG. 5A). No significant repression is noted with a control hybrid pair (AraC/Fos-LexA; FIG. 5B). FIG. 5A also shows that repression decreases as expression of fos-lexA from the tet promoter is reduced. The results suggest that our strategies can successfully improve repression with any pair of interaction domains. The dependence of repression on the relative amounts of the AraC and LexA hybrids also provides a third line of evidence that repression reflects heterodimerization.

Interaction cloning

Our system detects the interaction between domains of the HPV E6 and human E6AP proteins that interact in the yeast two-hybrid system. Huibregtse et al. (1991), *EMBO J.* 10: 4129–35. With 0.5 mM IPTG to induce E6AP-AraC$_{DNA}$, and 50 ng/ml of anhydrotetracycline to induce E6-LexA, we obtain a repression ratio of at least 30-fold. Repression is essentially absent with the non-interacting control pair AraC$_{DNA}$/E6-LexA or when the LexA operator is deleted from the P3IHFLexAimpX reporter plasmid (repression ratios of about 1.5 in each case). On solid medium with the LacZ indicator X-gal, repression with E6AP-AraC$_{DNA}$/E6-LexA generates pale blue colonies whereas dark blue colonies result with the controls. To evaluate if this signal differential can be exploited for interaction cloning, we mixed a BamH1 E6 fragment with an approximately 100-fold molar excess of total BamH1 digested *E. coli* chromosomal DNA. The mixture was ligated into the BamH1 site at the 3' end of lexA in our LexA expression vector where the correctly oriented E6 DNA is predicted to be in frame with lexA. After transformation into the reporter strain containing E6AP-AraC$_{DNA}$ construct, more than 95% of the transformants were blue on media with X-gal, 0.5 mM IPTG and 50 ng/ml AT. The remaining white colonies presumably contained the LexA-E6 fusion or they resulted from loss of the reporter plasmid which appears to occur at a low frequency. To avoid picking colonies that have lost the reporter gene and to try to specifically isolate colonies with LexA-E6 fusions, we picked 12 white colonies that eventually slowly turned blue. To further enrich for colonies containing LexA-E6 hybrids, plasmid DNA from all 12 colonies was pooled, retransformed into the reporter strain and plated exactly as above. The majority of transformants were now pale blue and PCR mapping of 16 randomly isolated pale blue transformants showed that all contained the E6AP coding fragment in the correct orientation behind lexA. The results show that a simple protocol can be used to efficiently isolate specific interactors of the AraC fusion partner by interaction cloning when only approximately 1 in 200 clones is expected to contain the E6-fragment fused to lexA in the correct orientation.

DISCUSSION

The *E. coli* two-hybrid system described here signals heterodimerization of AraC and LexA hybrids through repression of a lacZ reporter gene. Repression clearly requires two-hybrid interaction because noncognate hybrid pairs do not generate repression and because interaction cloning with E6AP-AraC as a bait could be used to specifically isolate E6 from an E6-spiked DNA library fused behind LexA. Repression also requires the LexA site and can be further enhanced by IHF betwen the AraC and LexA operators of the reporter plasmid, suggesting the involvement of DNA looping between operator-bound and heterodimeric hybrids (FIG. 3). Large repression loops should be less dependent on IHF because large loops bend and twist more easily (Rippe et al. (1995), *Trends in Biochem. Sci.* 20: 500–506. 35; Wang & Giaever (1988), *Science* 240: 300–306) and we have shown that IHF enhances repression with P3LexAOpX (small loop size of about 77 bp), but not with P3LexAOpH (large loop size of about 140 bp) (Table I). IHF-mediated DNA looping normally modulates promoter activity at other bacterial loci (Nash (1990) *Trends Biochem. Sci.* 15: 222–7; Pratt et al. (1996) *Mol. Microbiol.* 20: 911–7; Hoover et al. (1990) *Cell* 63: 11–22). The involvement of IHF in these distinct systems suggests that it functions as an independent module, thus providing a rationale for its effect in the artificial context of the *E. coli* two-hybrid system.

Figure 6:
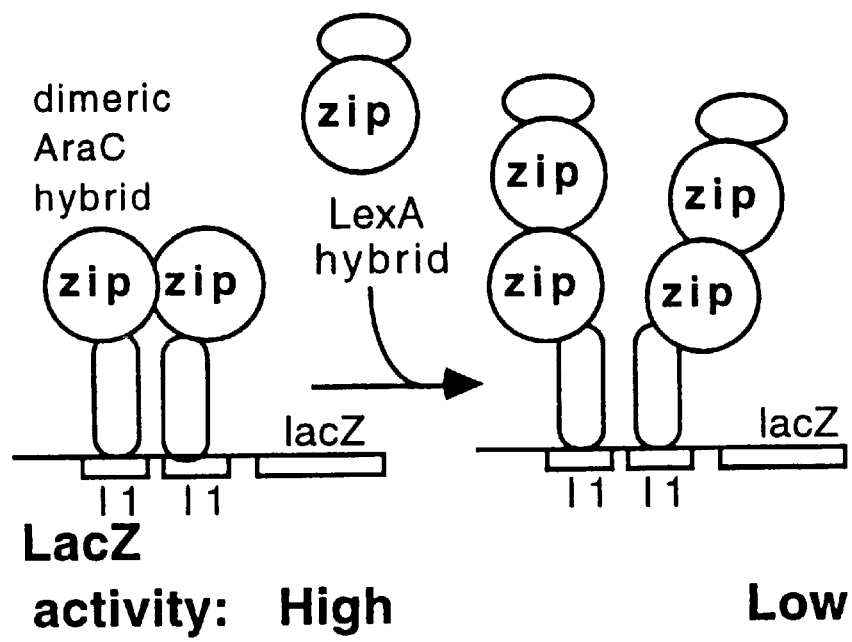
FIG. 6: Diagram of disruption of dimeric AraC hybrids through heterodimerization with LexA hybrids. See text for details.

Repression may reflect exclusion of RNAP from the promoter inside the loop (Mueller et al. (1996), *J. Mol. Biol.* 257: 21–9; Choy & Adhya (1992), *Proc. Natl. Acad. Sci. U.S.A.* 89: 11264–8; Huo et al. (1988), *Proc. Natl. Acad. Sci. U.S.A.* 85: 5444–8). A second mechanism of repression is suggested by the two-fold repression with zip-AraC$_{DNA}$/zip-LexA$_{DNA}$ and the P3 reporter plasmid (Table I). Since dimeric AraC molecules activate araBAD more efficiently from I1—I1 than monomeric AraC molecules (Reeder, T. & Schleif, R. (1993) *J. Mol. Biol.* 231: 205–218), zip-LexA$_{DNA}$ appears to cause repression with P3 by disrupting dimeric zip-AraC$_{DNA}$ through heterodimerization (FIG. 6). Consistent with this interpretation, Fos-AraC$_{DNA}$ is monomeric and Jun-LexA$_{DNA}$ fails to repress with plasmid P3 (Table I). Hybrid interaction-dependent DNA looping may also cause repression by altering DNA bending of the araBAD promoter region (Nickerson & Achberger (1995), *J. Bacteriol.* 177: 5756–61), or it may reflect physical interference of the repression loop (Chatterjee et al. (1997), *Proc. Natl. Acad. Sci. U.S.A.* 94: 2957–62) or the operator-bound LexA hybrid (Elledge & Davis (1989), *Genes & Dev.* 3: 185–197) with the activation functions of DNA-bound AraC or RNAP. Indeed, the geometry of AraC-RNAP interactions is likely to be complex because of the involvement of the RNAP α-subunit (Giffard & Booth (1988), *Mol. Gen. Genet.* 214: 148–152). The involvement of AraC-α interactions may explain why we were unable to achieve activation with our AraC/LexA hybrid heterodimers.

General utility of the *E. coli* two-hybrid system.

All AraC$_{DNA}$ hybrids in this report retain the ability to activate the araBAD promoter. We have also noted activation with larger fusion partners from the human papilloma virus E2 protein (Mueller & Sapp (1996), *Virology* 219: 247–256) and the eucaryotic DP1 (Girling et al. (1993), *Nature* 352: 83–87) and E47 (Kadesch (1993), *Cell Growth & Different.* 4: 49–55) proteins. Some fusion partners abolish the ability of AraC$_{DNA}$ to activate, but we generally observe good activation with fusions to the N-termini of wild-type AraC or zip-AraC$_{DNA}$. These findings are consistent with the organization of AraC into activation and dimerization domains (Eustance et al. (1994), *J. Mol. Biol.* 242: 330–338) and they suggest that AraC hybrids with an intact activation function can be obtained with most fusion partners. The suitability of LexA for generating hybrid proteins with good LexA operator binding ability is well documented (e.g. Allen et al. (1995), *Trends in Biochem. Sci.* 20: 511–16).

Some eucaryotic proteins fail to properly fold in *E. coli* (Cleland (1993) in *Protein Folding: in Vivo and in Vitro,* ed. J. Cleland (ACS), pp. 1–21) and this represents a potential limitation. We believe the system will prove to be particularly useful with procaryotic proteins, eucaryotic proteins that can be obtained in active form from *E. coli,* and smaller defined domains of eucaryotic proteins such as the E6/E6AP protein pair.

Mechanistically, the system differs fundamentally from the yeast two-hybrid system where protein interaction is indicated by reporter gene activation, but like the yeast system, it can detect homo- and heterodimeric interactions as demonstrated with the zip/zip and Fos/Jun protein pairs. These features distinguish these two systems from other *E. coli* systems that principally detect homodimeric interactions (Doerr et al. (1991) *Biochem.* 30, 9657–9664; Marchetti et al. (1995) *J. Mol. Biol.* 248, 541–550; Jappelli & Brenner (1996) *J. Mol. Biol.* 259, 575–578). The DNA loop between the AraC and LexA operators may be a key factor that contributes to the effectiveness of our two-hybrid system. Theoretical considerations (Rippe et al. (1995), *Trends in Biochem. Sci.* 20: 500–506; Wang & Giaever (1988), *Science* 240: 300–306) suggest that twisting and bending of a DNA loop reduces steric constraints that may prevent heterodimer subunits from binding closely adjacent half sites. This flexibility is a feature that is missing in the *E. coli* systems that detect protein homodimerization.

The potential for large interaction-dependent variations in reporter gene activity points to the basic usefulness of the system for the same applications for which the yeast two-hybrid system has been extensively used. These applications include the mapping of protein interaction domains and 'interaction cloning' and we have shown here that the current system version is probably adequate for isolating interactors from small insert libraries prepared from bacterial or yeast genomes. Replacement of the lac reporter gene with a gene whose expression is toxic (Wall (1996), *Bio Techniques* 20: 690–693), or the use of a toxic substrate for β-galactosidase (Davis & Jacob (1968) *J. Mol. Biol.* 36: 413–27), should permit positive selection of interacting clones from large mammalian insert libraries fused to LexA. Another application, the high-throughput screening for therapeutically active small molecule modulators of protein interactions (Gibbs & Oliff (1994) *Cell* 79: 193–198), may benefit from the faster growth rate and increased permeability of mutant *E. coli* strains (Higgins (1993) *Curr. Opin. in*

Cell Biol., 5: 684–687; Nakamura & Suganuma (1972) J. Bacteriol. 110: 329–35). Furthermore, E. coli does not require nuclear localization of hybrid proteins which has been problematic with non-nuclear target proteins in yeast (reviewed in Allen et al. (1995), Trends in Biochem. Sci. 20: 511–16). We believe that the system described here is a useful alternative to another E. coli system, which is mechanistically entirely different from the system described here, and for which applications similar to those of the yeast two-hybrid system have been proposed (Dove et al. (1997), Nature 386: 627–30).

TABLE 1

Summary of repression ratios with hybrid pairs containing cognate interaction domains. See text for calculation of ratios. 'AraC' and 'LexA' refer to the DNA binding domains of these proteins.

| | Reporter Construct | | | |
|---|---|---|---|---|
| | P3 | P3 LexAOpH | P3IHF LexAOpH | P3 LexAOpX | P3IHF LexAOpX |
| zip-AraC zip-LexA | 2.1 | 4.9 | 4.1 | 2.2 | 7.5 |
| Fos-AraC Jun-AraC | 1.1 | 2.0 | 1.9 | 2.3 | 4.2 |

TABLE 2

Summary of repression ratios with hybrid pairs predicted to be unable to interact. 'AraC' and 'LexA' are defined in Table 1.
AraC-wt = wild-type AraC.
ND = not determined.

| | Reporter Construct | | | |
|---|---|---|---|---|
| | P3 | P3 LexAOpH | P3IHF LexAOpH | P3 LexAOpX | P3IHF LexAOpX |
| AraC-wt zip-LexA | 1.2 | 1.1 | 1.0 | 1.2 | 1.2 |
| AraC zip-LexA | 1.2 | 1.00 | 1.1 | 1.1 | 1.2 |
| AraC Jun-LexA | ND | ND | ND | ND | 1.1 |

TABLE 3

Enhanced repression with reduced background reporter gene activity.
(A) Summary of background Miller units of Lac activities generated by plasmid P3 and the reporter plasmids of Table 1.
(B) Repression by zip-AraC$_{DNA}$/zip-LeXA$_{DNA}$ and control hybrid pairs with the P3IHFLexAOPmH reporter plasmid. AraC, LexA and AraC(wt) are as in FIG. 4.

| | | Reporter Construct | | | |
|---|---|---|---|---|---|
| A | | P3 | P3 LexAOpH | P3IHF LexAOpH | P3 LexAOpX | P3IHF LexAOpX |
| Miller Units | | 36 | 300 | 290 | 270 | 160 |

| | Hybrid Pair | | | |
|---|---|---|---|---|
| | zip-AraC + zip-LexA | AraC + zip-LexA | AraC (wt) + zip-LexA | AraC + Jun-LexA |
| B | | | | |
| repr ratio with P3IHF-LexAOpmH | 53 | 0.9 | 1.06 | 1.09 |

| | |
|---|---|
| AT | anhydrotetracycline |
| bp | base pairs |
| CPRG | Chlorophenolred-β-D galactopyranoside |
| cDNA | complementary DNA |
| DNA | deoxyribonucleic acid |
| IFTG | isopropylthiogalactoside |
| kb, kbp | kilobase pairs |
| MU | Miller units |
| RNA | ribonucleic acid |
| wt | wild type |

What is claimed is:

1. A prokaryotic host cell comprising:
   (a) a fusion protein having
      (i) a first DNA-binding domain and
      (ii) a first protein-interacting domain;
   (b) a fusion protein having
      (i) a second DNA-binding domain and
      (ii) a second protein-interacting domain which binds to the first interacting domain; and
   (c) a nucleic acid molecule having a reporter gene operatively linked to
      (i) a promoter,
      (ii) a first operator site which binds to the first DNA-binding domain, located upstream of the promoter, and
      (iii) a second operator site which binds the second DNA-binding domain, located downstream of the promoter and the first operator site;
   wherein binding of the first interacting domain to the second interacting domain is signaled by altered expression of the reporter gene.

2. A process for detecting inhibition or enhancement of binding of a first interacting domain with a second interacting domain, which process comprises:
   (a) providing at least one host cell according to claim 1;
   (b) treating said at least one host cell with a test substance, and
   (c) screening for altered expression of the reporter gene, wherein detection of altered expression of the reporter gene indicates inhibition or enhancement of binding of the first interacting domain with the second interacting domain.

3. The cell of claim 1, wherein:
   (a) the first DNA-binding domain is an AraC DNA binding domain,
   (b) the first operator site is an AraC operator site,
   (c) the second DNA-binding domain is a LexA DNA binding domain, and
   (d) the second operator site is a LexA operator site.

4. The cell of claim 1, wherein the nucleic acid molecule further comprises more than one second operator site operatively linked to the reporter gene.

5. The cell of claim 1, wherein the reporter gene is selected from nucleic acids encoding β-galactosidase, antibiotic resistance genes, and toxic genes.

6. The cell of claim 1, wherein the cell is a bacterial cell.

7. The cell of claim 1, wherein the cell is an E. coli cell.

8. The process of claim 2, wherein:
   (a) the first DNA-binding domain is an AraC DNA binding domain,
   (b) the first operator site is an AraC operator site,
   (c) the second DNA-binding domain is a LexA DNA binding domain, and
   (d) the second operator site is a LexA operator site.

9. The process of claim 2, wherein the nucleic acid molecule further comprises more than one second operator site operatively linked to the reporter gene.

10. The process of claim 2, wherein the reporter gene is selected from nucleic acids encoding β-galactosidase, antibiotic resistance genes, and toxic genes.

11. The process of claim 2, wherein the cell is a bacterial cell.

12. The process of claim 2, wherein the cell is an E. coli cell.

13. A nucleic acid having a reporter gene operatively linked to
   (a) an AraC operator site,
   (b) a promoter, and
   (c) a LexA operator site.

14. A reporter vector comprising the nucleic acid of claim 13.

15. The nucleic acid molecule of claim 13, further comprising more than one LexA operator half site operatively linked to the reporter gene.

16. The nucleic acid of claim 13, wherein the reporter gene is selected from nucleic acids encoding β-galactosidase, antibiotic resistance genes, and toxic genes.

17. A reporter vector comprising the nucleic acid of claim 15.

18. A reporter vector comprising the nucleic acid of claim 16.

19. A process for detecting a cell comprising a test domain that interacts with a known domain, which comprises:
   (1) generating a library of cells in which each cell comprises:
      (a) a fusion protein having
         (i) a first DNA-binding domain and
         (ii) a known domain;
      (b) a fusion protein having
         (i) a second DNA-binding domain and
         (ii) a test domain; and
      (c) a nucleic acid molecule having a reporter gene operatively linked to
         (i) a promoter,
         (ii) a first operator site which binds to the first DNA-binding domain, located upstream of the promoter, and (iii) a second operator site which binds the second DNA-binding domain, located downstream of the promoter of the reporter gene;

(2) detecting cells exhibiting altered expression of the reporter gene, which signals interaction between the known domain and the test domain.

20. The process of claim 19, wherein:
(a) the first DNA-binding domain is an AraC DNA binding domain,
(b) the first operator site is an AraC operator site,
(c) the second DNA-binding domain is a LexA DNA binding domain, and
(d) the second operator site is a LexA operator site.

21. The process of claim 19, wherein the nucleic acid molecule further comprises more than one second operator site operatively linked to the reporter gene.

22. The process of claim 19, wherein the reporter gene is selected from nucleic acids encoding β-galactosidase, antibiotic resistance gene, and toxic genes.

23. The process of claim 19, wherein the cell is a bacterial cell.

24. The process of claim 19, wherein the cell is an *E. coli* cell.

* * * * *